United States Patent
Choi

(10) Patent No.: US 8,343,331 B2
(45) Date of Patent: Jan. 1, 2013

(54) METHOD FOR CORRECTING ERRONEOUS RESULTS OF MEASUREMENT IN BIOSENSORS AND APPARATUS USING THE SAME

(75) Inventor: In Hwan Choi, Suwon-si (KR)

(73) Assignee: Philosys Co., Ltd., Gunsan-si, Jeollabuk-do (KR)

( * ) Notice: Subject to any disclaimer, the term of this patent is extended or adjusted under 35 U.S.C. 154(b) by 343 days.

(21) Appl. No.: 12/670,900

(22) PCT Filed: Sep. 26, 2008

(86) PCT No.: PCT/KR2008/005708
§ 371 (c)(1),
(2), (4) Date: Jan. 27, 2010

(87) PCT Pub. No.: WO2009/041782
PCT Pub. Date: Apr. 2, 2009

(65) Prior Publication Data
US 2010/0206749 A1    Aug. 19, 2010

(30) Foreign Application Priority Data

Sep. 27, 2007 (KR) ........................ 10-2007-0097198

(51) Int. Cl.
*G01N 27/327* (2006.01)
(52) U.S. Cl. .................. 205/777.5; 205/789; 205/792; 422/68.1; 435/14
(58) Field of Classification Search ..... 204/400–403.15; 205/777.5, 787, 792, 775, 789; 600/309–367; 422/68, 68.1; 435/14
See application file for complete search history.

(56) References Cited

U.S. PATENT DOCUMENTS

| 3,828,260 | A | 8/1974 | Underwood |
| 4,547,735 | A | 10/1985 | Kiesewetter et al. |
| 5,385,846 | A | 1/1995 | Kuhn et al. |

(Continued)

FOREIGN PATENT DOCUMENTS

| EP | 1691192 A1 | 8/2006 |
| KR | 10-2006-0019442 A | 3/2006 |

OTHER PUBLICATIONS

Mostert et al. (Anestheisology, vol. 1, No. 29, 1968, 145-147).*
Abbott Point of Care Manual (pp. 1-8)('Abbott').*

*Primary Examiner* — J. Christopher Ball
*Assistant Examiner* — Jennifer Dieterle
(74) *Attorney, Agent, or Firm* — Lucas & Mercanti, LLP

(57) ABSTRACT

Disclosed herein is a method of correcting erroneous measurement results in a biosensor. The method includes the steps of: (a) applying a first voltage from a voltage generator 12 to a test strip 10 when a blood sample is applied on the test strip 10, and measuring an electric current generated from the test strip within one second of applying the first voltage by a microcontroller unit (MCU), and then calculating a hematocrit value of the blood sample using the measured electric current value! (b) applying a second voltage from the voltage generator to the test strip after calculating the hematocrit value of the blood sample, and measuring an electric current generated from the test strip within a predetermined time of applying the second voltage, and then calculating a glucose level using the measured electric current value; and (c) correcting the glucose level in (b) by using the calculated hematocrit value in (a).

5 Claims, 7 Drawing Sheets

U.S. PATENT DOCUMENTS

| | | |
|---|---|---|
| 6,805,780 B1 | 10/2004 | Ryu et al. |
| 2004/0157339 A1* | 8/2004 | Burke et al. .................. 436/149 |
| 2004/0232009 A1* | 11/2004 | Okuda et al. .................. 205/789 |
| 2006/0275890 A1* | 12/2006 | Neel et al. .................. 435/287.2 |
| 2007/0154951 A1* | 7/2007 | Kermani ........................ 435/7.1 |
| 2007/0270774 A1* | 11/2007 | Bergman et al. .............. 604/361 |

* cited by examiner

[Figure 1]
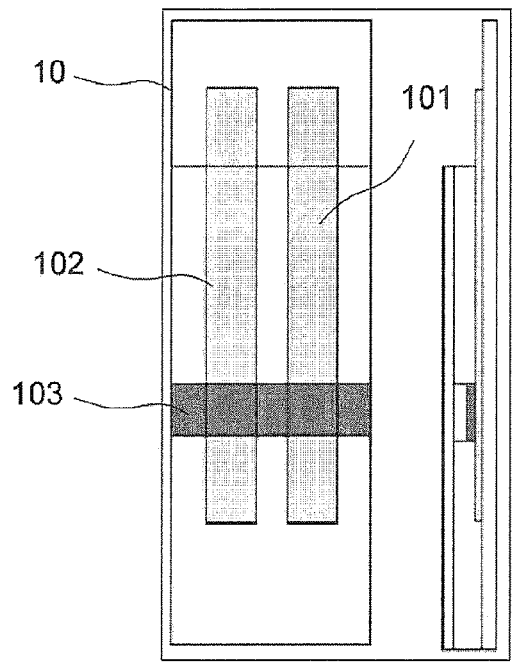
[Figure 2]
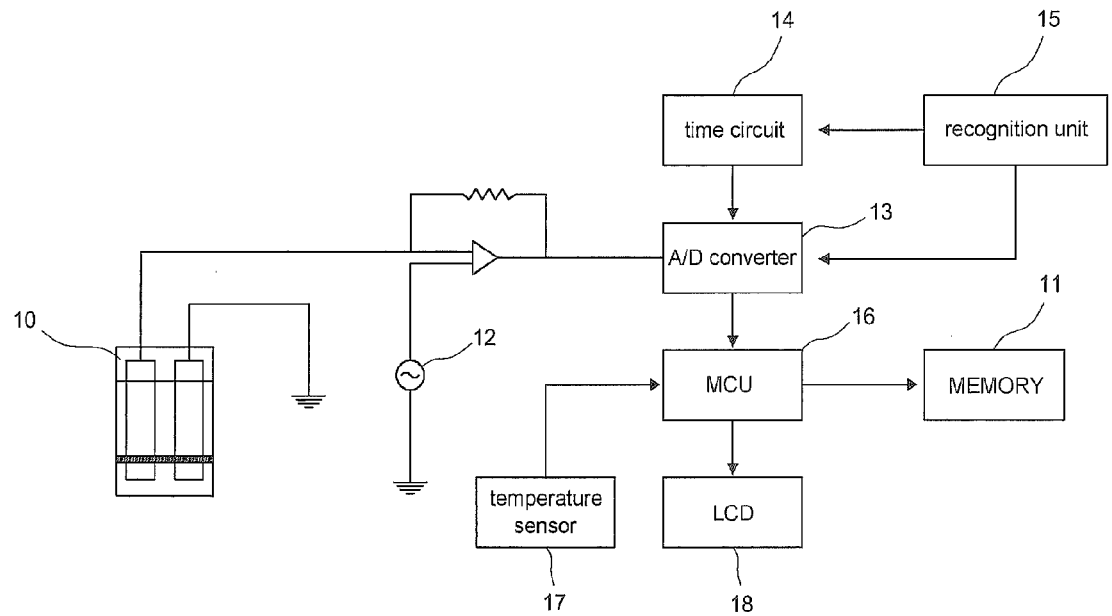

[Figure 3]
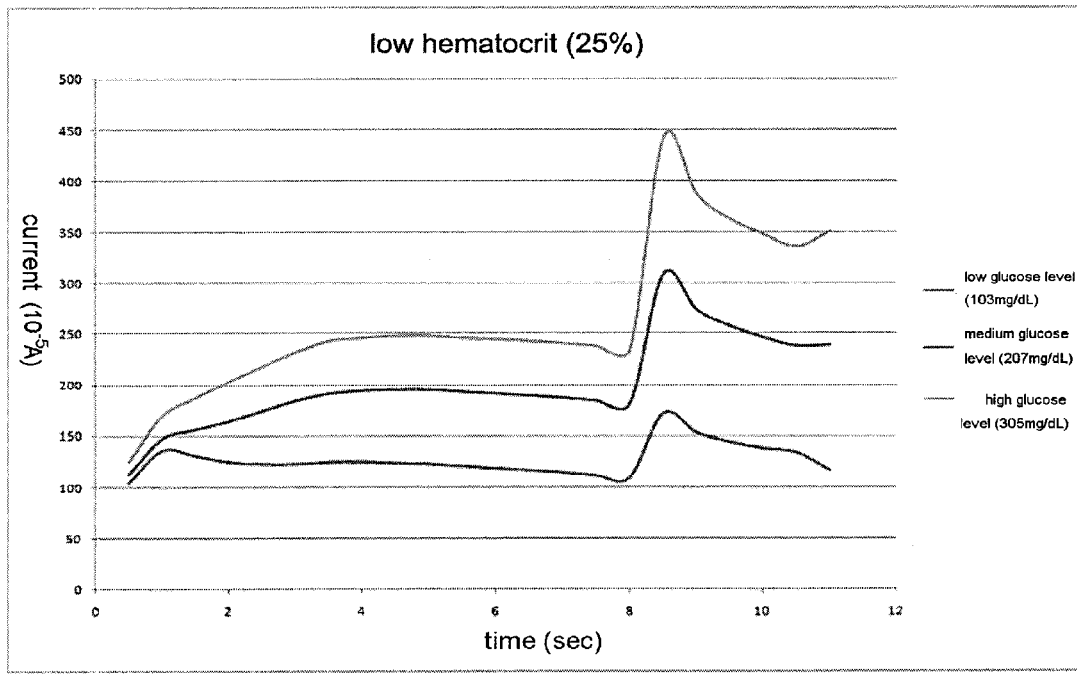
[Figure 4]
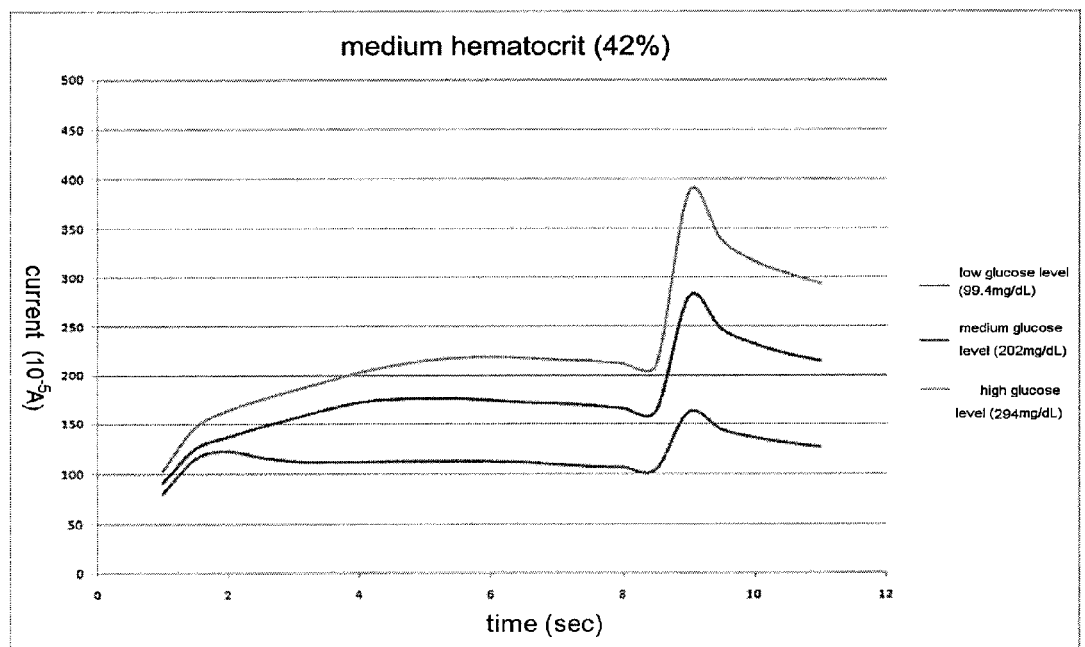

[Figure 5]
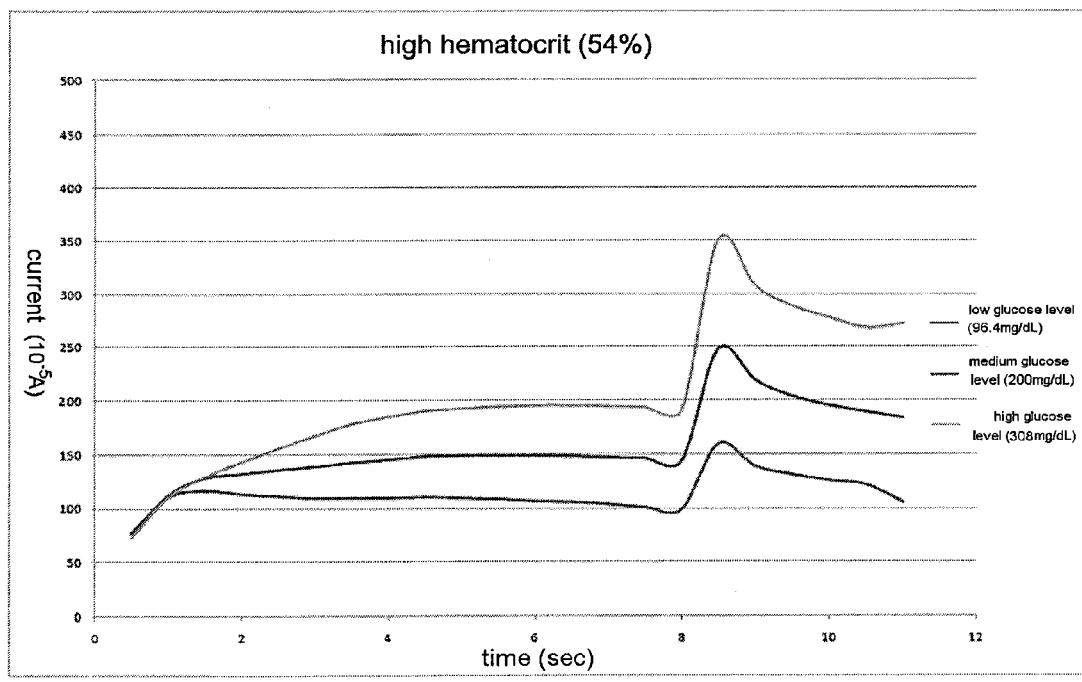

[Figure 6]
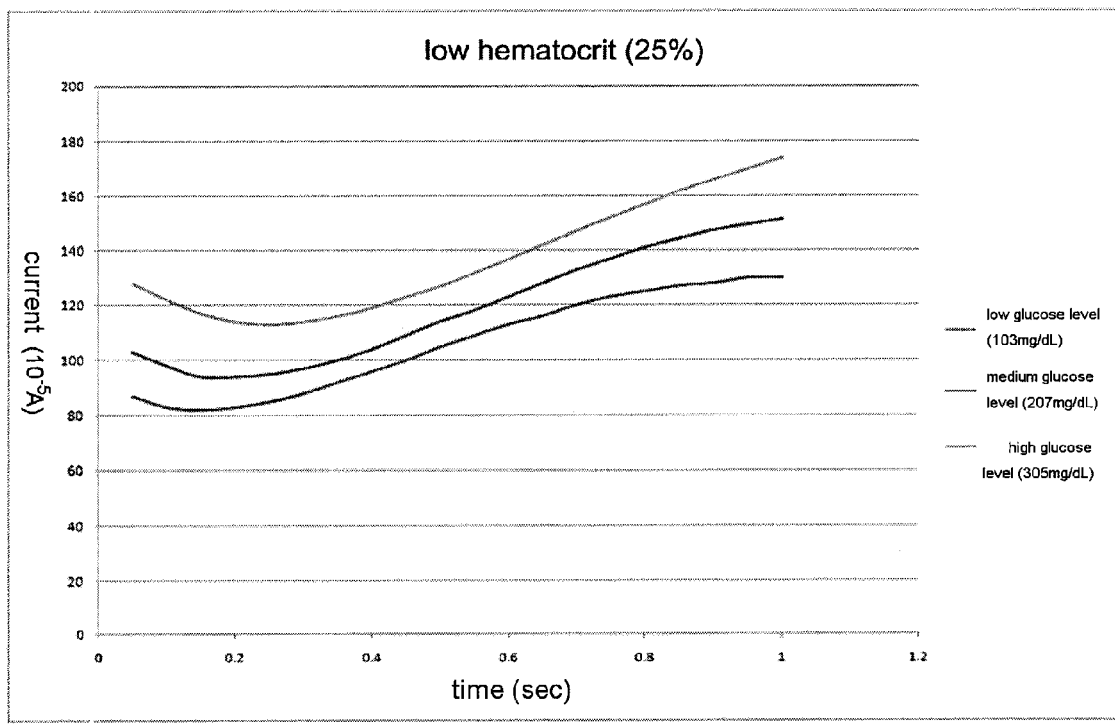

[Figure 7]
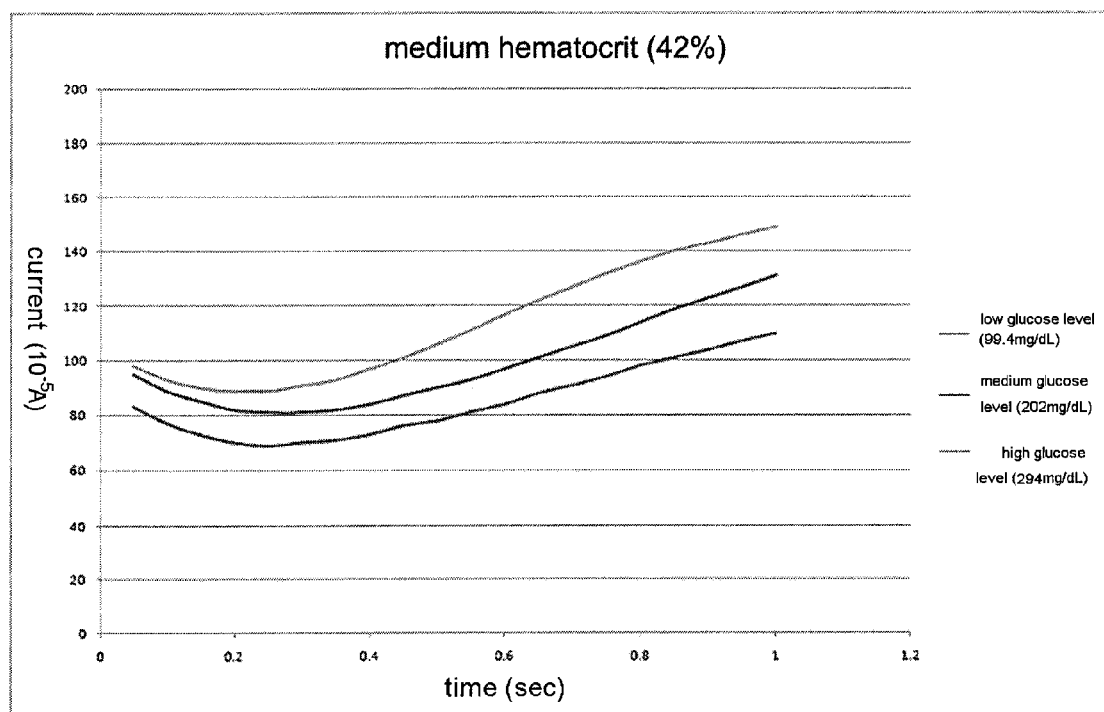

[Figure 8]
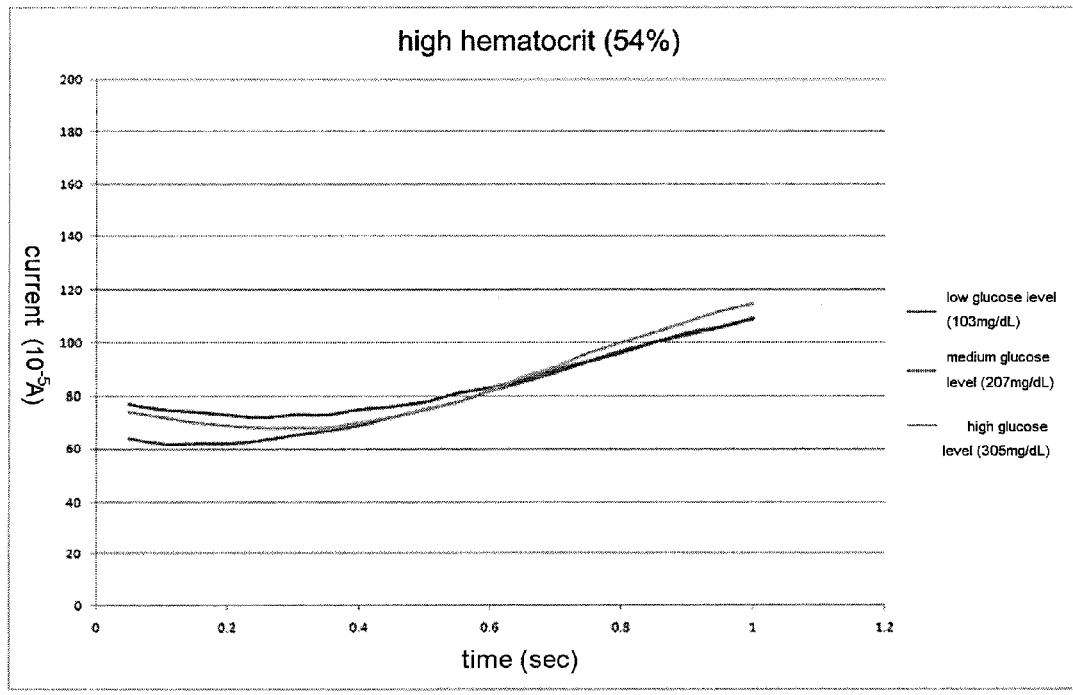
[Figure 9]
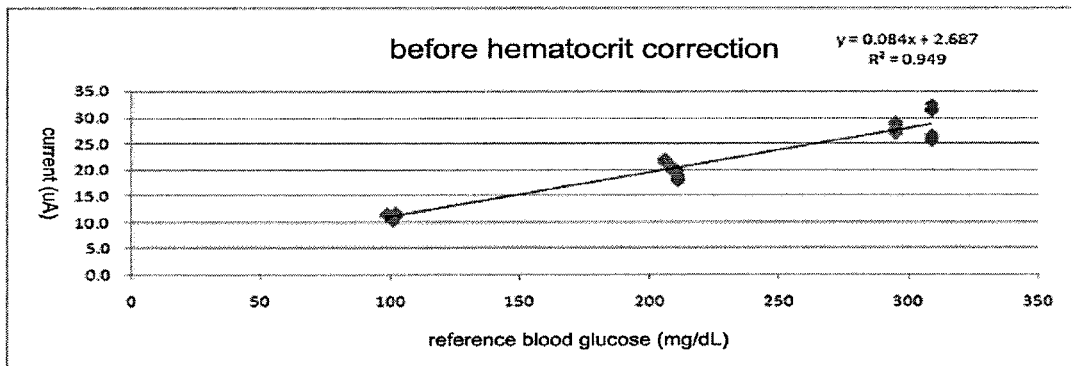

[Figure 10]
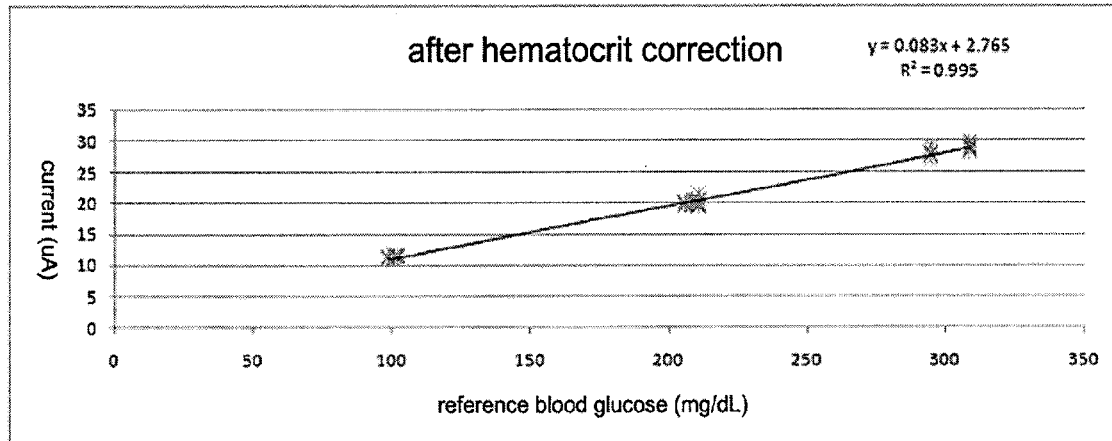
[Figure 11]
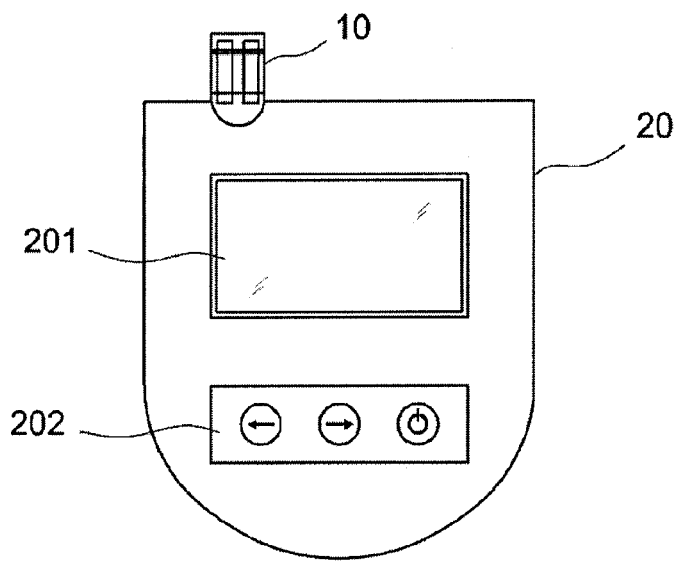

METHOD FOR CORRECTING ERRONEOUS RESULTS OF MEASUREMENT IN BIOSENSORS AND APPARATUS USING THE SAME

CROSS-REFERENCE TO RELATED APPLICATION

This application is a 371 of PCT/KR2008/005708 filed on Sep. 26, 2008, which claims the benefit of Korean Patent Application No. 10-2007-0097198 filed on Sep. 27, 2007, the contents of each of which are incorporated herein by reference.

TECHNICAL FIELD

The present invention relates to a method of correcting erroneous measurement results in a biosensor and an apparatus using the same. More particularly, the present invention relates to a method of correcting erroneous measurement results caused by hematocrit and humidity when quantitatively determining blood glucose level by a biosensor using a biochemical test strip, and an apparatus using the same.

BACKGROUND ART

The present invention relates to a method of improving the accuracy of blood glucose level measurement by a biosensor using a biochemical test stripe, and an apparatus using the same.

Specifically, when quantitative determining blood glucose level, it is well known that hematocrit, humidity, temperature, and other interfering substances are main factors which adversely affect on the accuracy of glucose level measurement in blood. Although temperature is the most influential factor, correction of the effect caused by temperature is implemented in most biosensors. In the meantime, although many studies have been undertaken thus far to correct the effect caused by hematocrit which is a less affecting factor on the glucose level measurement than temperature, there is no method yet that could substantially improve on the accuracy of glucose level measurement. Thus, a diagnostic device which can accurately determine the glucose level in blood by using a method which can offset the effects caused by hematocrit and humidity is desirable.

Hematocrit generally refers to the proportion of blood that consists of packed red blood cells, which is expressed as a percentage by volume, while humidity refers to the amount of moisture absorbed in conventional test strips. On average, hematocrit of adults normally ranges from 35 to 45%, while it can be 60% or more as shown in pregnant women, newborns and smokers, and 30% or less in people having anemia or other diseases. The effect of hematocrit on the glucose level measurement can be significant in people with hematocrit less than 30% or greater than 60%.

Many studies have been undertaken to offset the effects these elements have on the glucose level measurement, as much efforts have been put into research for minimizing the effects caused by temperature and hematocrit. However, so far no attempts have been made on the development of a correction algorithm for correcting erroneous measurement results caused by hematocrit in blood glucose level measuring devices.

Most studies on measurement and correction methods to offset the effect caused by hematocrit have been based on the Coulter principle which Wallace H. Coulter discloses in U.S. Pat. No. 2,656,508. Methods of measuring hematocrit level may be classified into a resistance measurement method and an electrical conductivity measurement method which are also based on the Coulter principle, except for non-invasive methods such as ultrasonography and optical sensor methods.

U.S. Pat. No. 3,250,987 discloses a meter for measuring the volume concentration of red blood cells by using the fact that red blood cells act like a nonconductor of electricity in a certain range of frequency, and measuring the conductivity of diluted blood correlated to the total amount of red blood cells and thus hematocrit value.

U.S. Pat. No. 3,828,260 discloses a hematocrit measuring apparatus in which hematocrit value is measured by detecting the change of current correlated to the increase of impedance which occurs when diluted blood is flown through small pipe, since blood corpuscle is regarded as an impedance factor in this invention.

U.S. Pat. No. 4,547,735 discloses an instrument for measuring hematocrit value of blood, in which two electrodes are placed in a horizontal plane. When blood sample is inserted into the instrument, hematocrit value is calculated by measuring the change of impedance in blood.

U.S. Pat. No. 5,385,846 discloses a method for determining the hematocrit level of blood by using an electrochemical sensor strip to measure the conductivity of blood. The method comprises applying 500 mV of potential difference sufficient to oxidize a reactant on a test strip to generate current 20 seconds after blood sample is applied to the test strip, and measuring the current by amperometry.

However, the aforementioned inventions have disadvantages in that a long correction time is required to offset the effect of hematocrit and that they have low accuracy. Also error correction methods depending on the blood types are not disclosed therein. Consequently, even though measurements are conducted for a long time, reliable measurements which can be used to accurately diagnose physiological abnormalities in patients cannot be obtained and the measurement are still off by the effects of hematocrit and humidity.

Korean Patent No. 10-591246 discloses a test strip for an electrochemical biosensor that can compensate the effect of hematocrit by using a red blood cell interference corrective.

Although the above invention has an advantage in that the effect of hematocrit is reduced compared to conventional methods since red blood cells are hemolyzed chemically by a red blood cell interference corrective, it still has a drawback in that the amount of blood flown in the test strip is different from the original amount present before the red blood cells are hemolyzed.

Furthermore, when the red blood cell interference corrective is used in the test strip, it oxidizes the mediator which is needed to measure the blood glucose level when using electrochemical methods, such that the test strip has low time stability.

As such, conventional methods and apparatuses for measuring the blood glucose level usually have a long correction time and low accuracy. Also, in the case of using the red blood cell interference corrective, it is ineffective to correct erroneous measurements caused by the effect of hematocrit because red blood cells are hemolyzed such that hematocrit value cannot be measured accurately.

On the other hand, in the case of venous blood, the measured blood glucose level tends to be lower than reference values, while it tends to be higher than reference values in capillary blood. However, this phenomenon is not reflected in the correction by the conventional measuring methods.

Accordingly, the inventor of the present invention has developed a method of correcting erroneous measurements caused by the effect of hematocrit in a biosensor, in which an algorithmic error correction method is used according to the blood types such as capillary blood and venous blood in order to obtain accurate blood glucose level measurements. The method has additional advantages in terms of cost since it eliminates the need for additional instruments, and in terms of stability since the method also eliminates the need to apply reagents to conventional test strips, which prolongs the stability of the strips with respect to time.

DISCLOSURE

Technical Problem

An object of the present invention is to provide a method of correcting measured values in a biosensor and an apparatus using the same by analyzing the change in the value of current on the electrochemical test strip and by correlating the relationship between current and a hematocrit value.

Another object of the present invention is to provide an algorithmic correction method which offsets the effect caused by hematocrit to improve the accuracy of blood glucose level measured by a biosensor, and an apparatus using the same.

Another object of the present invention is to provide a method of correcting measured values in a biosensor and an apparatus using the same by determining whether the blood is capillary blood or venous blood and then applying a different algorithmic equation according to the determined result.

Another object of the present invention is to provide a method of minimizing the effects of hematocrit and humidity have on blood glucose level measured by a biosensor and an apparatus using the same.

Another object of the present invention is to provide a method of correcting measured values in a biosensor, which reduces cost by eliminating the need for additional instruments and provides stability in test strips by eliminating the need to apply reagents to conventional test strips, which prolong the stability of the strips with respect to time.

Other objects and advantages of this invention will be apparent from the ensuing disclosure and appended claims.

Technical Solution

One aspect of the invention provides a method of correcting an erroneous measurement result in a biosensor, the method including the steps of: (a) applying a first voltage from a voltage generator 12 to a test strip 10 when a blood sample is applied on the test strip 10, and measuring an electric current generated from the test strip within one second of applying the first voltage by a microcontroller unit (MCU), and then calculating a hematocrit value of the blood sample using the measured electric current value; (b) applying a second voltage from the voltage generator 12 to the test strip 10 after calculating the hematocrit value, and measuring an electric current generated from the test strip within a predetermined time of applying the second voltage, and then calculating a glucose level using the measured electric current value; and (c) correcting the glucose level in (b) by using the calculated hematocrit value in (a).

Another aspect of the present invention provides a biosensor including: a test strip 10 for measuring a glucose level; a voltage generator 12; an analog-to-digital (A/D) converter 13 for converting an analogue signal of a measured voltage to a digital signal; a recognition unit 15 which detects whether a blood sample has been applied on the test strip 10 and controls the A/D converter 13; a microcontroller unit (MCU) 16 which stores, controls and executes a program for performing the methods of correcting erroneous measurement results; a time circuit 14 which controls the voltage generator 12 and the MCU 16 to detect a voltage of a digital signal output from the A/D converter 13; a liquid crystal display (LCD) 18 which displays a blood glucose level after error correction; and a memory 11 which stores a value corresponding to the blood glucose level displayed on the LCD 18.

DESCRIPTION OF DRAWINGS

FIG. 1 is a perspective view illustrating a biochemical test strip used for measuring blood glucose level.

FIG. 2 is a schematic view and a block diagram illustrating operation of a biosensor system according to the present invention.

FIG. 3 is a graph illustrating the change in electric currents in blood samples of low hematocrit (25%) respectively having low, medium and high blood glucose levels.

FIG. 4 is a graph illustrating the change in electric currents in blood samples of medium hematocrit (42%) respectively having low, medium and high blood glucose levels.

FIG. 5 is a graph illustrating the change in electric currents in blood samples of high hematocrit (54%) respectively having low, medium and high blood glucose levels.

FIG. 6 is a graph illustrating the change in electric currents in the blood samples of low hematocrit (25%) respectively having low, medium and high blood glucose levels for a first second shown in FIG. 3.

FIG. 7 is a graph illustrating the change in electric currents in the blood samples of medium hematocrit (42%) respectively having low, medium and high blood glucose levels for a first second shown in FIG. 4.

FIG. 8 is a graph illustrating the change in electric currents in the blood samples of high hematocrit (54%) respectively having low, medium and high blood glucose levels for a first second shown in FIG. 5.

FIG. 9 is a graph showing the distribution of electric current values to reference blood glucose level values before applying a correction algorithm in accordance with the present invention.

FIG. 10 is a graph showing the distribution of electric current values to the reference glucose level values after applying the correction algorithm in accordance with the present invention.

FIG. 11 is a schematic view of a biosensor with a test strip inserted therein according to an embodiment of the present invention.

The present invention now will be described more fully hereinafter in the following detailed description of the invention.

BEST MODE

The present invention relates to a method of correcting erroneous measurement results in a biosensor and an apparatus using the same and, more particularly, to a method of increasing the accuracy of blood glucose level measurements by offsetting the effect of hematocrit has on measured blood glucose level in a simple way, and apparatus using the same method.

FIG. 1 is a perspective view illustrating a biochemical test strip used for measuring blood glucose level. The test strip includes a working electrode 102 and a reference electrode 101. An electrochemical substance 103 is provided below the test strip in a form of a strip attached across the working electrode 102 and the reference electrode 101. The electrochemical substance includes glucose oxidase and potassium ferricyanide. When a blood sample is applied on the electrochemical substance, glucose in the blood sample is oxidized and ferricyanide is deoxidized into ferrocyanide. When a voltage is applied, a potential difference is formed between the two electrodes, and the amount of electrons proportional to the glucose level in the blood sample flow out of the working electrode of the test strip to form a current.

FIG. 2 is a schematic view and a block diagram illustrating operation of a biosensor system according to the present invention.

An operating mechanism for measuring hematocrit value and offsetting the effect of hematocrit on blood glucose level in a glucose measuring device of the present invention will be described below. First, the glucose measuring device indicates a signal to apply blood on the test strip. A recognition unit 15 detects a signal output from an A/D converter 13. If the detected signal has a voltage greater than a predetermined voltage, the recognition unit 15 determines that the blood is applied on the test strip, and then initiates a time circuit 14 in order to start a test. At this time, a voltage generator 12 starts to operate, and the voltage generator generates voltage of 10 to 150 mV, preferably 40 to 120 mV (a first voltage). The time circuit 14 operates a microcontroller unit (MCU) 16 to detect a voltage of a signal output from the A/D converter 13 within one second of applying the first voltage by the voltage generator 12, preferably 200 to 550 msec, more preferably 450 to 530 msec. The detected voltage is converted to a current value, and then a hematocrit value is calculated by a current-hematocrit correlation equation stored in the MCU 16.

0.1 to 2.5 seconds, preferably 1.5 seconds after the hematocrit values are calculated, the time circuit 14 operates the voltage generator 12 to generate a voltage of 200 to 600 mV, preferably 250 to 350 mV (a second voltage). Immediately after or within a predetermined amount of time of applying the second voltage, the time circuit 14 operates the MCU 16 to detect a voltage of a signal output from the A/D converter 13. A time period for detecting the voltage value from the A/D converter 13 may be preferably two to three seconds of generating the second voltage, more preferably 2.5 to 3 seconds of generating the second voltage. However, it should be apparent that various changes and modifications of the time period of detecting the voltage of a signal output from the A/D converter 13 can easily be carried out by those ordinarily skilled in the art without departing from the spirit and scope of the present invention.

The detected voltage of a signal output from the A/D converter 13 is then converted to a current value, and the current value is used for calculating a hematocrit value by the current-hematocrit correlation equation stored in the MCU 16. The detailed description of the current-hematocrit correlation equation will be elaborated below. The calculated hematocrit values are then used in a correction equation in order to obtain a hematocrit corrected blood glucose level.

Here, since a mechanism about the way in which hematocrit in blood reacts with the electrochemical test strip used in the present invention has not been fully disclosed so far, the error caused by the effect of hematocrit may not be easy to analyze. Nevertheless, since objects of the present invention is to minimize or reduce the effect of hematocrit when measuring blood glucose level using the test strip, it is necessary to determine the correlation between hematocrit and electrochemical substance of the test strip. More particularly, it is important to determine the correlation between the current value and the hematocrit value of a blood sample through the variation in the amount of current generated from the reaction of glucose in the blood sample and the electrochemical substance of the test strip.

In the present invention, amperometry is used as one of electrochemical methods. The reference voltage of an electrochemical compound is dependent on the energy level of the electrochemical compound. When a potential greater than the reference voltage is applied in a solution having the electrochemical compound, oxidation occurs to generate electrons. On the contrary, when a negative potential less than the reference voltage is applied, reduction occurs. The amperometry is a method for determining the amount of a substance to be measured in the electrochemical compound by measuring the variation in the amount of current proportional to the amount of electrons flowed from the substance as a result of a potential difference generated by a voltage applied to the electrochemical compound.

The variation in the amount of current generated from the oxidation-reduction reactions which take place between the blood and the electrochemical compound attached to the electrode of the test strip is correlated to the hematocrit value in blood. In order to determine the correlation, an operation is carried out as described below.

First, a first voltage of 50 mV is applied to the working electrode and the reference electrode, and an analog signal of measured voltage is converted to a digital signal by an A/D converter at 500 msec. The measured voltage value of the digital signal is then changed to a current value which may be used to determine the blood types. After a time interval of 1.5 seconds when no voltage is applied to the two electrodes, a second voltage of 300 mV is applied for 3 seconds. Voltage of a digital signal output from the A/D converter is detected at 2.5 seconds of applying the second voltage. Current flowing through the working electrode of the test strip within these time ranges is calculated using the following equation 1, and thus graphs shown in FIGS. 3 to 8 can be obtained from the above method. Here, the load resistance of an OP amp is may vary depending on the devices used and can be easily varied by those ordinary skilled in the art.

$$\text{Current flowing through the working electrode} = \frac{(\text{applied voltage} - \text{measured voltage})}{\text{load resistance of an } OPamp} \times 10[\mu A] \quad \text{(Equation 1)}$$

FIGS. 3 to 5 are graphs illustrating the change in electric currents in blood samples of low, medium and high hematocrit values respectively having low, medium and high glucose levels. More particularly, FIGS. 3 to 5 respectively correspond to blood samples having a low hematocrit value of 25%, a medium hematocrit value of 45% and a high hematocrit value of 60%. With respect to each hematocrit level, the changes in electric currents in the blood samples respectively having low, medium and high glucose levels according to time are shown in FIGS. 3 to 5. FIGS. 6 to 8 are graphs illustrating the change in electric currents in the blood samples of low, medium and high hematocrit values respectively having low, medium and high glucose levels for a first second shown respectively in FIG. 3, FIG. 4, and FIG. 5. The unit of the current values in FIGS. 3 to 8 is $10^{-5}$ A. As shown in FIGS. 6 to 8, although the current values are different according to different hematocrit values and different glucose levels, it can be seen that a relatively small difference exists within a time range of 300 to 700 msec. Accordingly, current values measured for blood samples respectively having different glucose levels within the time range of 300 to 700 msec are very similar to each other, and it can be determined that hematocrit values calculated by using the current measured within this time range are indifferent to different glucose levels.

Therefore, it can be determined that a current value measured after applying the first voltage is the current value that is affected by hematocrit in a blood sample, and that a current value measured after applying the second voltage is the current value corresponding to the glucose level after chemical reactions in the blood sample have been finished on the test strip. As a result, the effect of hematocrit on the glucose level of the blood sample can be minimized by adjusting the current values.

The present invention is carried out by measuring the current value within the time range of from 300 to 700 msec which is most affected by hematocrit, and which is least affected by different glucose levels of blood samples, calculating a hematocrit value using the equation with the measured current value, and correcting the measured glucose level value using another equation with the calculated hematocrit value.

In order to obtain the equation for calculating a hematocrit value, a current is measured within one second of applying the first voltage after preparing blood samples having respectively low, medium and high glucose level, and then a slope and an intercept are estimated on X-axis representing electric current and Y-axis representing hematocrit. In an exemplary embodiment, after blood samples respectively having 100 mg/dL, 150 mg/dL, and 250 mg/dL of glucose level are prepared at hematocrit levels of 25%, 45%, and 65%, the current values at 500 msec are measured. The above process may be carried out for capillary blood and venous blood respectively, and then current-hematocrit equation set forth in the following Equation 2, specifically Equations 6 to 11, can be obtained. In the following Equation 2, m and n are experimentally determined coefficients, and they are dependent on the glucose level.

In the following Table 1, glucose concentration values in a standard blood sample and reference values of hematocrit thereof, and current values obtained from standard blood samples at 500 msec are set forth. The values in Table 1 may be used as reference values to glucose concentration values, hematocrit values, and current values measured at 500 msec, which are standard values of hematocrit and glucose level. The method of obtaining the glucose level values may be easily carried out by those ordinary skilled in the art.

TABLE 1

| | Glucose level | | | | | | | | |
|---|---|---|---|---|---|---|---|---|---|
| | 103 | 994 | 964 | 207 | 202 | 200 | 305 | 294 | 308 |
| Hematocrit | 25% | 40% | 55% | 25% | 40% | 55% | 25% | 40% | 55% |
| $I_{0.5t}$ | 105 | 80 | 77 | 113 | 91 | 77 | 125 | 103 | 73 |

(a unit of a glucose value is mg/dL, and a unit of current is $10^{-5}$ A.)

$$\text{Hct}(\%) = m*I_{0.5t} + n \quad \text{(Equation 2)}$$

wherein, $I_{0.5t}$ is a measured current value at 500 msec.

Another aspect of the present invention provides a method of correcting hematocrit effect according to whether blood is capillary blood or venous blood, which can be distinguished from a current value measured at the point of 500 msec ($I_{0.5t}$). The determining method will be described below. Hematocrit value difference between equations applied to venous and capillary blood occurs due to different oxygen saturation in venous and capillary blood. Specifically, capillary blood having high oxygen saturation also has high hematocrit value. It is important to apply different equation according to whether blood is capillary blood or venous blood, since glucose level measured in venous blood is estimated lower than the reference value, and glucose level measured in capillary blood is estimated to be higher than the reference value. Here, it is important for the measured values to be adjusted appropriately to obtain accurate results. Furthermore, although conventional glucose test meters have been used for measuring glucose level of capillary blood, there has been an increasing need for measuring glucose level of venous blood. The conventional glucose test meters for home use have been used for an initial screening purpose in many hospitals, while venous blood is widely used for many diagnostic tests.

After a hematocrit value is calculated by the current-hematocrit equation, hematocrit effect is finally corrected by using a correction equation with the calculated hematocrit value. The correction equation is represented in the following Equation 3. In Equation 3, Glc2 is a measured glucose level value before correcting the effect of hematocrit and Glc2' is a calculated glucose level value after correcting the effect of hematocrit, and γ is a variable dependent on the hematocrit value calculated from Equation 2. However, δ can be easily modified by those skilled in the art in a range of from −10 to +10 depending on the experimental conditions.

$$\text{Glc2'} = \text{Glc2}*\gamma + \delta \quad \text{(Equation 3)}$$

wherein, $\gamma = (45 - \text{Hct}(\%))*0.075$, $\delta = 1$,

Glc2 is a measured glucose value before correcting a hematocrit effect, and Glc2' is a calculated glucose value after correcting a hematocrit effect.

In an exemplary embodiment, the present invention further comprises a process of correcting humidity effect in addition to correcting hematocrit effect. The present invention provides an algorithmic correction method of correcting the effect of humidity. Humidity is another factor affecting the glucose level measurement since current value which correlates to the glucose level is sensitive to humidity. Specifically, in most test strips, current increases as humidity increases. That is, current value is almost zero under dry condition. The values of current flown through the electrodes of test strips according to various humidity percentages are shown in the following Table 2. It can be seen that as humidity increases, current value also increases.

TABLE 2

| | Humidity | | | | |
|---|---|---|---|---|---|
| | 10% | 30% | 50% | 70% | 80% |
| Current value | 0.21 uA | 0.82 uA | 1.42 uA | 2.02 uA | 2.32 uA |

The humidity correction may be performed either before or after the hematocrit correction. However, when the humidity correction is performed before the hematocrit correction, a corrected glucose value obtained from the humidity correction may be used in the hematocrit correction. For example, the corrected glucose value obtained from the humidity correction may be used as the measured glucose level value before correcting the effect caused by hematocrit (Glc2) in Equation 3 to perform the subsequent correction.

The method of correcting humidity effect includes applying voltage to the test strip 10 by the voltage generator 12, converting an electric current flown through the test strip 10 to a voltage, converting an analogue signal of the converted voltage to a digital signal by the A/D converter 13, and calculating a humidity value by the MCU 16 using the following Equation 4 which is stored therein, and then correcting a glucose level value by using the following Equation 5 with the calculated humidity value.

$$\text{Humidity (\%)} = x * Inosample + y \quad \text{(Equation 4)}$$

wherein, Inosample is a current value measured when the blood sample is not applied to the test strip.

$$Glc1' = Glc1 * \alpha + \beta \quad \text{(Equation 5)}$$

wherein, $\alpha = (55 - \text{Humidity (\%)}) * 0.005$, $\beta = 1$,

Glc1 is a measured glucose value before correcting a humidity effect, and Glc1' is a calculated glucose value after correcting a humidity effect.

In Equation 4, x and y are unknowns which are determined experimentally. In Equation 5, Glc1 is a measured glucose concentration value before correcting the effect caused by humidity, Glc1' is a calculated glucose level value after correcting the effect caused by humidity, and α is a variable dependent on the humidity value calculated from Equation 4. However, β can be easily modified by those skilled in the art in a range of from −10 to +10 depending on the experimental conditions.

A resulting glucose level value corrected in accordance with the above method is displayed on an LCD 18 and stored in a memory unit 11, and after determining whether the test strip is removed from the biosensor, the test ends if the test strip is removed.

Another aspect of the present invention provides an apparatus for measuring blood glucose level using the above algorithmic correction methods. FIG. 11 illustrates a biosensor with a test strip inserted therein according to an embodiment of the present invention. When a blood sample is applied to the test strip 10, glucose level is measured by the biosensor 20. The measured glucose level is displayed on an LCD screen 201, and user may control operations or check memories stored by controlling a throttle 202.

The method of obtaining the correction algorithms described above may be applied to various test strips. Although other correction algorithms having different coefficients may be obtained depending on the type of test strips, the same method as in the present invention can be applied to obtain correction algorithms. Therefore, the present invention provides a method which can increase the accuracy of glucose level measurements and which reduces cost by eliminating the need for additional instruments and provides long-term stability in test strips by no use of reagents to conventional test strips, which prolongs the stability of the strips with respect to time.

The invention may be better understood by reference to the following examples which are intended for the purpose of illustration and are not to be construed as in any way limiting the scope of the present invention, which is defined in the claims appended hereto.

MODE FOR INVENTION

Examples

When a blood sample was applied on the test strip 10, 50 mV was applied to the working electrode and the reference electrode of the test strip 10, and the voltage of a digital signal output from 8th pin of U2C OP-AMP (as an A/D converter) was measured. 1.5 seconds later, 300 mV was applied to the working electrode. Then, 3 seconds later, a current flown on the test strip was measured, and a corrected glucose level was calculated by solving the following equations with the measured current value.

Obtaining Equation for Calculating Hematocrit in Venous Blood

Equations for calculating hematocrit in venous blood were obtained from repeated experiments, based on the above Table 1. After venous blood samples respectively having 100 mg/dL, 150 mg/dL and 250 mg/dL of glucose levels were prepared at hematocrit values of 25%, 45% and 65%, current values at 500 msec were obtained and shown in the following Table 3.

TABLE 3

|  | Hct 25% | Hct 45% | Hct 65% |
|---|---|---|---|
| 100 mg/dL | 107 | 84.2 | 61.5 |
| 150 mg/dL | 114.56 | 91.1 | 67.6 |
| 250 mg/dL | 124.5 | 93.4 | 62.2 |

(a unit of current is $10^{-5}$ A.)

Then, the following Equations 6 to 8 which were set forth according to glucose levels were obtained from estimating a slope and an intercept, while X-axis represents an electric current and Y-axis represents hematocrit.

1) if a glucose level of the blood sample is less than 150

$$\text{Hct (\%)} = -0.8788 * I_{0.5t} + 119 \quad \text{(Equation 6)}$$

2) if a glucose level of the blood sample is in a range of from 150 to 250

$$\text{Hct (\%)} = -0.8514 * I_{0.5t} + 122 \quad \text{(Equation 7)}$$

3) if a glucose level of the blood sample is greater than 250

$$\text{Hct (\%)} = -0.6426 * I_{0.5t} + 105 \quad \text{(Equation 8)}$$

wherein, $I_{0.5t}$ is a measured current value at 500 msec, and a unit thereof is $10^{-5}$ A.

Obtaining Equation for Calculating Hematocrit in Capillary Blood

Equations for calculating hematocrit in capillary blood were obtained from repeated experiments, based on Table 1. After capillary blood samples respectively having 100 mg/dL, 150 mg/dL and 250 mg/dL of glucose levels were prepared at the hematocrit values of 25%, 45% and 65%, current values at 500 msec were obtained and shown in the following Table 4.

TABLE 4

|  | Hct 25% | Hct 45% | Hct 65% |
|---|---|---|---|
| 100 mg/dL | 180.93 | 158.2 | 135.4 |
| 150 mg/dL | 190.3 | 166.8 | 143.3 |
| 250 mg/dL | 225.6 | 194.5 | 163.4 |

(a unit of current is $10^{-5}$ A.)

Then, the following Equations 9 to 11 which were set forth according to glucose levels were obtained from estimating a slope and an intercept, while X-axis represents an electric current and Y-axis represents hematocrit.

1) if a glucose level of the blood sample is less than 150

$$\text{Hct (\%)} = -0.8788 * I_{0.5t} + 184 \quad \text{(Equation 9)}$$

2) if a glucose level of the blood sample is in a range of from 150 to 250

$$\text{Hct (\%)} = -0.8514 * I_{0.5t} + 187 \quad \text{(Equation 10)}<$$

3) if a glucose level of the blood sample is greater than 250

$$\text{Hct (\%)} = -0.6426 * I_{0.5t} + 170 \quad \text{(Equation 11)}$$

wherein, $I_{0.5t}$ is a measured current value at 500 msec, and a unit thereof is $10^{-5}$ A Determination of Whether Blood is Capillary or Venous Blood from Current Value Whether blood is capillary or venous blood was determined from a current value at 500 msec ($I_{0.5t}$). In the equations described above, when $I_{0.5t}$ was greater than 160, blood was determined as capillary blood, and when $I_{0.5t}$ was less than 160, blood was determined as venous blood. Here, if the current value is 160 in equations 6 to 8, a hematocrit value may be less than 5 which is not a possible result in venous blood.

Calculation of Corrected Glucose Concentration

A corrected glucose concentration value was obtained by measuring current values within the time interval at which only hematocrit had an effect on the current values and when glucose level had minimum or no effect on the current values, and calculating a hematocrit value by using Equations 6 to 11, after determining whether the blood was capillary or venous blood, and then solving correction algorithm as defined in the following Equation 3 using the calculated hematocrit value.

$$Glc2'=Glc2*\gamma+\delta \qquad \text{(Equation 3)}$$

wherein, $\gamma=(45-Hct (\%))*0.075$, $\delta=1$,

Glc2 is a measured glucose value before correcting a hematocrit effect, and Glc2' is a calculated glucose value after correcting a hematocrit effect.

Correction Algorithm for Offsetting the Effect of Humidity

Coefficients of the correction algorithm for offsetting the effect of humidity were obtained from repeated experiments, based on the above Table 2. When a blood sample was not applied on an uncontaminated test strip, humidity value (%) of the test strip was calculated by using the current-humidity relationship in the following Equation 12, and the measured glucose level was then corrected by using the following Equation 5 with the calculated humidity value.

$$\text{Humidity (\%)}=33.173*I\text{nosample}+2.885 \qquad \text{(Equation 12)}$$

wherein, Inosample is a current value measured when the blood sample is not applied to the test strip.

$$Glc1'=Glc1*\alpha+\beta \qquad \text{(Equation 5)}$$

wherein, $\alpha=(55-\text{Humidity (\%)})*0.005$, $\beta=1$,

Glc1 is a measured glucose value before correcting a humidity effect, and Glc1' is a calculated glucose value after correcting a humidity effect.

FIGS. 9 and 10 are graphs respectively showing the distribution of electronic current values to the reference glucose level values before and after applying of the correction algorithm, in which the correction effect according to the present invention is shown. FIG. 10 is a graph showing a relationship between the measured current value and the reference glucose level values after applying the correction algorithm of the present invention, while FIG. 9 is a graph showing a relationship between the measured current value and the reference glucose level values before applying the correction algorithm of the present invention. As shown in FIG. 9, the current is measured to be about 9 to 13 µA at a concentration of 100 mg/dL, about 17 to 23 µA at a concentration of 210 mg/dL, and about 24 to 34 µA at a concentration of 300 mg/dL, it can be seen that the deviation of the current values increases as the glucose level increases. In contrast, FIG. 10 exhibits little deviation regardless of increasing glucose level.

A comparison of graphs in FIG. 9 and FIG. 10 shows that the readings taken after applying the method of correcting glucose level value of the present invention are highly accurate since glucose level value in FIG. 10 exhibits little deviation from the slant line.

As a result, the present invention provides an accurate method of correcting measured blood glucose levels in a biosensor by applying correction algorithms obtained from analyzing the change in currents flown from the electrochemical test strip and determining correlation of the currents to hematocrit values. The present invention also has advantages in that different algorithm can be used depending on whether a blood sample is from capillary or venous blood, thereby a more accurate blood glucose level can be obtained, and that the error correction method makes it possible to reduces cost by eliminating the need for additional instruments and provides long-term stability in test strips.

In the above, the present invention was described based on the specific preferred embodiments, but it should be apparent to those ordinarily skilled in the art that various changes and modifications can be added without departing from the spirit and scope of the present invention which will be defined in the appended claims.

The invention claimed is:

1. A method of correcting erroneous measurement results in a biosensor, the method comprising the steps of:
    (a) applying a first voltage from a voltage generator 12 to a test strip 10 when a blood sample is applied on the test strip 10, and measuring an electric current generated from the test strip within one second of applying the first voltage by a micro controller unit (MCU), and then calculating a hematocrit value of the blood sample using the measured electric current value;
    (b) applying a second voltage from the voltage generator 12 to the test strip 10 after calculating the hematocrit value of the blood sample, and measuring an electric current generated from the test strip within a predetermined time of applying the second voltage, and then calculating a glucose level using the measured electric current value; and
    (c) correcting the glucose level in (b) by using the calculated hematocrit value in (a),
    wherein
    the step of calculating of the hematocrit value of the blood sample in (a) comprises calculating a hematocrit value using the following Equation 2, the following Equation 2 being obtained by preparing blood samples respectively having low, medium and high glucose levels corresponding to low, medium and high hematocrit values, measuring an electric current at 500 msec for each blood sample, and by estimating a slope and an intercept with X-axis representing an electric current, and Y-axis representing hematocrit:

$$Hct(\%)=m*I_{0.5t}+n \qquad \text{(Equation 2)}$$

wherein, $I_{0.5t}$ is a measured current value at 500 msec, and m and n are experimentally determined coefficients; and the step of correcting of the glucose concentration value in (c) is performed by using the following Equation 3:

$$Glc2'=Glc2*\gamma+\delta \qquad \text{(Equation 3)}$$

wherein,
$\gamma=(45-Hct(\%))*0.075$, $\delta=1$;
Glc2 is a measured glucose value before correcting a hematocrit effect; and
Glc2' is a calculated glucose value after correcting a hematocrit effect.

2. The method of claim 1, wherein said electric current generated from the test strip within one second is an electric current generated from the test strip within 450 to 530 msec.

3. The method of claim 1, wherein the step of calculating of the hematocrit value of the blood sample in (a) is performed by using the following Equation 6 if the blood sample is determined to be from venous blood and a glucose level thereof is less than 150 mg/dL, by using the following Equation 7 if the blood sample is determined to be from venous blood and a glucose level thereof is in a range of from 150 mg/dL to 250 mg/dL, or by using the following Equation 8 if the blood sample is determined to be from venous blood and a glucose level thereof is greater than 250 mg/dL:

1) if a glucose level of the blood sample is less than 150 mg/dL $$\text{Hct (\%)} = -0.8788 * I_{0.5t} + 119 \quad \text{(Equation 6)}$$

2) if a glucose level of the blood sample is in a range of from 150 mg/dL to 250 mg/dL $$\text{Hct (\%)} = -0.8514 * I_{0.5t} + 122 \quad \text{(Equation 7)}$$

3) if a glucose level of the blood sample is greater than 250 mg/dL $$\text{Hct (\%)} = -0.6426 * I_{0.5t} + 105 \quad \text{(Equation 8)}$$

wherein, $I_{0.5t}$ is a measured current value at 500 msec, and a unit thereof is $10^{-5}$ A and the step of correcting of the glucose level value in (c) is performed by using the following Equation 3:

$$\text{Glc2'} = \text{Glc2} * \gamma + \delta \quad \text{(Equation 3)}$$

wherein, $\gamma = (45 - \text{Hct (\%)}) * 0.075$, $\delta = 1$,

Glc2 is a measured glucose value before correcting a hematocrit effect, and

Glc2' is a calculated glucose value after correcting a hematocrit effect.

4. The method of claim 1, wherein the step of calculating of the hematocrit value of the blood sample in (a) is performed by using the following Equation 9 if the blood sample is determined to be from capillary blood and a glucose thereof is less than 150 mg/dL, by using the following Equation 10 if the blood sample is determined to be from capillary blood and a glucose level thereof is in a range of from 150 mg/dL to 250 mg/dL, or by using the following Equation 11 if the blood sample is determined to be from capillary blood and a glucose level thereof is greater than 250 mg/dL:

1) if a glucose level of the blood sample is less than 150 mg/dL $$\text{Hct (\%)} = -0.8788 * I_{0.5t} + 184 \quad \text{(Equation 9)}$$

2) if a glucose level of the blood sample is in a range of from 150 mg/dL to 250 mg/dL $$\text{Hct (\%)} = -0.8514 * I_{0.5t} + 187 \quad \text{(Equation 10)}$$

3) if a glucose level of the blood sample is greater than 250

$$\text{Hct (\%)} = -0.6426 * I_{0.5t} + 170 \quad \text{(Equation 11)}$$

wherein, $I_{0.5t}$ is a measured current value at 500 msec, and a unit thereof is $10^{-5}$ A, and wherein the step of correcting of the glucose level value in (c) is performed by using the following Equation 3:

$$\text{Glc2'} = \text{Glc2} * \gamma + \delta \quad \text{(Equation 3)}$$

wherein, $\gamma = (45 - \text{Hct (\%)}) * 0.075$, $\delta = 1$;

Glc2 is a measured glucose value before correcting a hematocrit effect; and

Glc2' is a calculated glucose value after correcting a hematocrit effect.

5. The method of claim 1, further comprising a step of correcting measurement results from an effect of humidity, wherein the step of correcting measurement results comprises the steps of:

applying a voltage from a voltage generator 12 to a test strip 10 before a blood sample is applied to the test strip 10;

converting an electric current generated through the test strip 10 to voltage and then converting an analogue signal of the converted voltage to a digital signal by an analog-to-digital (A/D) converter 13;

calculating a humidity value by the MCU 16; and correcting the glucose level value using the calculated humidity value, wherein the step of calculating a humidity value is performed by using the following Equation 12, and the step of correcting the glucose level value is performed by using the following Equation 5 with the calculated humidity value:

$$\text{Humidity (\%)} = 33.173 * I\text{nosample} + 2.885 \quad \text{(Equation 12)}$$

wherein,

Inosample is a current value measured when the blood sample is not applied to the test strip;

$$\text{Glc1'} = \text{Glc1} * \alpha + \beta \quad \text{(Equation 5)}$$

wherein, $\alpha = (55 - \text{Humidity (\%)}) * 0.005$, $\beta = 1$;

Glc1 is a measured glucose value before correcting a humidity effect, and

Glc1' is a calculated glucose value after correcting a humidity effect.

* * * * *